(12) United States Patent
Butts et al.

(10) Patent No.: US 7,594,910 B2
(45) Date of Patent: Sep. 29, 2009

(54) CATHETER CONNECTOR

(75) Inventors: M. David Butts, Draper, UT (US);
Jordan P. Diamond, Salt Lake City, UT (US); Ryan Patterson, Kaysville, UT (US); Guy Rome, West Valley, UT (US); Jason Stats, Woods Cross, UT (US); William R. Barron, Riverton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 288 days.

(21) Appl. No.: 10/803,279

(22) Filed: Mar. 18, 2004

(65) Prior Publication Data

US 2005/0209581 A1 Sep. 22, 2005

(51) Int. Cl.
*A61M 25/16* (2006.01)
(52) U.S. Cl. .................. 604/533; 604/523; 604/534; 604/905
(58) Field of Classification Search .............. 604/533, 604/534, 523, 171, 905
See application file for complete search history.

(56) References Cited

U.S. PATENT DOCUMENTS

| | | | |
|---|---|---|---|
| 3,921,631 A | 11/1975 | Thompson | |
| 4,123,091 A * | 10/1978 | Cosentino et al. | 285/39 |
| 4,134,402 A | 1/1979 | Mahurkar | |
| 4,340,052 A * | 7/1982 | Dennehey et al. | 604/317 |
| D272,651 S | 2/1984 | Mahurkar | |
| 4,432,759 A * | 2/1984 | Gross et al. | 604/411 |
| 4,539,003 A * | 9/1985 | Tucker | 604/93.01 |
| 4,543,087 A | 9/1985 | Sommercorn et al. | |
| 4,568,329 A | 2/1986 | Mahurkar | |
| 4,583,968 A | 4/1986 | Mahurkar | |
| 4,592,749 A | 6/1986 | Ebling et al. | |
| 4,596,571 A * | 6/1986 | Bellotti et al. | 604/411 |
| 4,623,327 A | 11/1986 | Mahurkar | |
| 4,643,711 A | 2/1987 | Bates | |
| 4,675,004 A | 6/1987 | Hadford et al. | |
| 4,681,122 A | 7/1987 | Winters et al. | |
| 4,682,978 A | 7/1987 | Martin | |
| 4,692,141 A | 9/1987 | Mahurkar | |
| 4,723,948 A * | 2/1988 | Clark et al. | 604/533 |
| 4,738,658 A | 4/1988 | Magro et al. | |
| 4,770,652 A | 9/1988 | Mahurkar | |
| 4,772,268 A | 9/1988 | Bates | |
| 4,808,155 A | 2/1989 | Mahurkar | |
| 4,842,582 A | 6/1989 | Mahurkar | |
| 4,895,561 A | 1/1990 | Mahurkar | |
| 5,053,003 A | 10/1991 | Dadson et al. | |
| 5,053,004 A | 10/1991 | Markel et al. | |
| 5,053,023 A | 10/1991 | Martin | |

(Continued)

FOREIGN PATENT DOCUMENTS

EP 183396 A1 * 6/1986

(Continued)

*Primary Examiner*—Nicholas D Lucchesi
*Assistant Examiner*—Laura A Bouchelle
(74) *Attorney, Agent, or Firm*—Rutan & Tucker LLP

(57) ABSTRACT

A catheter connector for a subcutaneously placed catheter. The catheter connector can be configured for a single lumen catheter or a multiple lumen catheter. The connector facilitates precise positioning of both distal and proximal ends of a catheter, providing enhanced functionality and patient comfort.

22 Claims, 18 Drawing Sheets

U.S. PATENT DOCUMENTS

| | | |
|---|---|---|
| 5,057,073 A | 10/1991 | Martin |
| 5,059,170 A | 10/1991 | Cameron |
| 5,135,599 A | 8/1992 | Martin et al. |
| 5,156,592 A | 10/1992 | Martin et al. |
| 5,188,593 A | 2/1993 | Martin |
| 5,190,520 A | 3/1993 | Fenton, Jr. et al. |
| 5,190,528 A * | 3/1993 | Fonger et al. ............... 604/171 |
| 5,195,962 A | 3/1993 | Martin et al. |
| 5,197,951 A | 3/1993 | Mahurkar |
| 5,207,650 A | 5/1993 | Martin |
| 5,209,723 A | 5/1993 | Twardowski et al. |
| 5,221,255 A | 6/1993 | Mahurkar |
| 5,221,256 A | 6/1993 | Mahurkar |
| 5,312,337 A | 5/1994 | Flaherty et al. |
| 5,324,274 A | 6/1994 | Martin |
| 5,342,386 A | 8/1994 | Trotta |
| 5,350,358 A | 9/1994 | Martin |
| 5,360,397 A | 11/1994 | Pinchuk |
| 5,374,245 A | 12/1994 | Mahurkar |
| 5,378,230 A | 1/1995 | Mahurkar |
| 5,380,276 A | 1/1995 | Miller et al. |
| 5,399,172 A | 3/1995 | Martin et al. |
| 5,405,320 A | 4/1995 | Twardowski et al. |
| 5,405,341 A | 4/1995 | Martin |
| 5,409,644 A | 4/1995 | Martin et al. |
| 5,417,668 A | 5/1995 | Setzer et al. |
| 5,454,409 A * | 10/1995 | McAffer et al. ............. 141/329 |
| 5,472,417 A | 12/1995 | Martin et al. |
| 5,472,432 A | 12/1995 | Martin |
| 5,480,380 A | 1/1996 | Martin |
| 5,486,159 A | 1/1996 | Mahurkar |
| 5,509,897 A | 4/1996 | Twardowski et al. |
| 5,569,182 A | 10/1996 | Twardowski et al. |
| 5,624,413 A | 4/1997 | Markel et al. |
| 5,685,867 A | 11/1997 | Twardowski et al. |
| 5,704,915 A | 1/1998 | Melsky et al. |
| 5,718,678 A | 2/1998 | Fleming, III |
| 5,772,643 A | 6/1998 | Howell et al. |
| 5,776,111 A | 7/1998 | Tesio |
| 5,797,869 A | 8/1998 | Martin et al. |
| 5,807,311 A | 9/1998 | Palestrant |
| 5,944,732 A | 8/1999 | Raulerson et al. |
| 5,961,485 A | 10/1999 | Martin |
| 5,961,486 A | 10/1999 | Twardowski et al. |
| 5,976,103 A | 11/1999 | Martin |
| 5,989,213 A | 11/1999 | Maginot |
| 6,074,374 A | 6/2000 | Fulton |
| 6,086,555 A | 7/2000 | Eliasen et al. |
| 6,099,519 A * | 8/2000 | Olsen et al. ................. 604/534 |
| 6,155,610 A * | 12/2000 | Godeau et al. .............. 285/242 |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,293,927 B1 | 9/2001 | McGuckin, Jr. |
| 6,332,874 B1 | 12/2001 | Eliasen et al. |
| 6,423,050 B1 | 7/2002 | Twardowski et al. |
| 6,508,807 B1 * | 1/2003 | Peters ........................ 604/533 |
| 6,592,565 B2 | 7/2003 | Twardowski et al. |
| 6,638,242 B2 | 10/2003 | Wilson et al. |
| 6,722,705 B2 | 4/2004 | Korkor |
| 7,163,531 B2 | 1/2007 | Seese et al. |
| 2001/0041857 A1 | 11/2001 | Sansoucy |
| 2002/0099326 A1 | 7/2002 | Wilson et al. |
| 2002/0099327 A1 | 7/2002 | Wilson et al. |
| 2003/0065288 A1* | 4/2003 | Brimhall et al. ........ 604/165.03 |
| 2003/0066218 A1 | 4/2003 | Schweikert et al. |
| 2003/0088213 A1 | 5/2003 | Schweikert et al. |
| 2003/0153898 A1 | 8/2003 | Schon et al. |
| 2003/0187411 A1 | 10/2003 | Constantz |
| 2003/0199853 A1 | 10/2003 | Olsen et al. |
| 2003/0201639 A1 | 10/2003 | Korkor |
| 2004/0097903 A1 | 5/2004 | Raulerson |
| 2004/0122418 A1 | 6/2004 | Voorhees |
| 2004/0183305 A1 | 9/2004 | Fisher |
| 2005/0085794 A1 | 4/2005 | Denoth et al. |
| 2005/0095891 A1 | 5/2005 | Schorn |

FOREIGN PATENT DOCUMENTS

| | | |
|---|---|---|
| WO | WO 02/058776 A2 | 8/2002 |
| WO | WO 02058776 A2 * | 8/2002 |
| WO | WO 03/030960 A2 | 4/2003 |
| WO | WO 03/030962 A2 | 4/2003 |
| WO | WO 03/033049 A2 | 4/2003 |

* cited by examiner

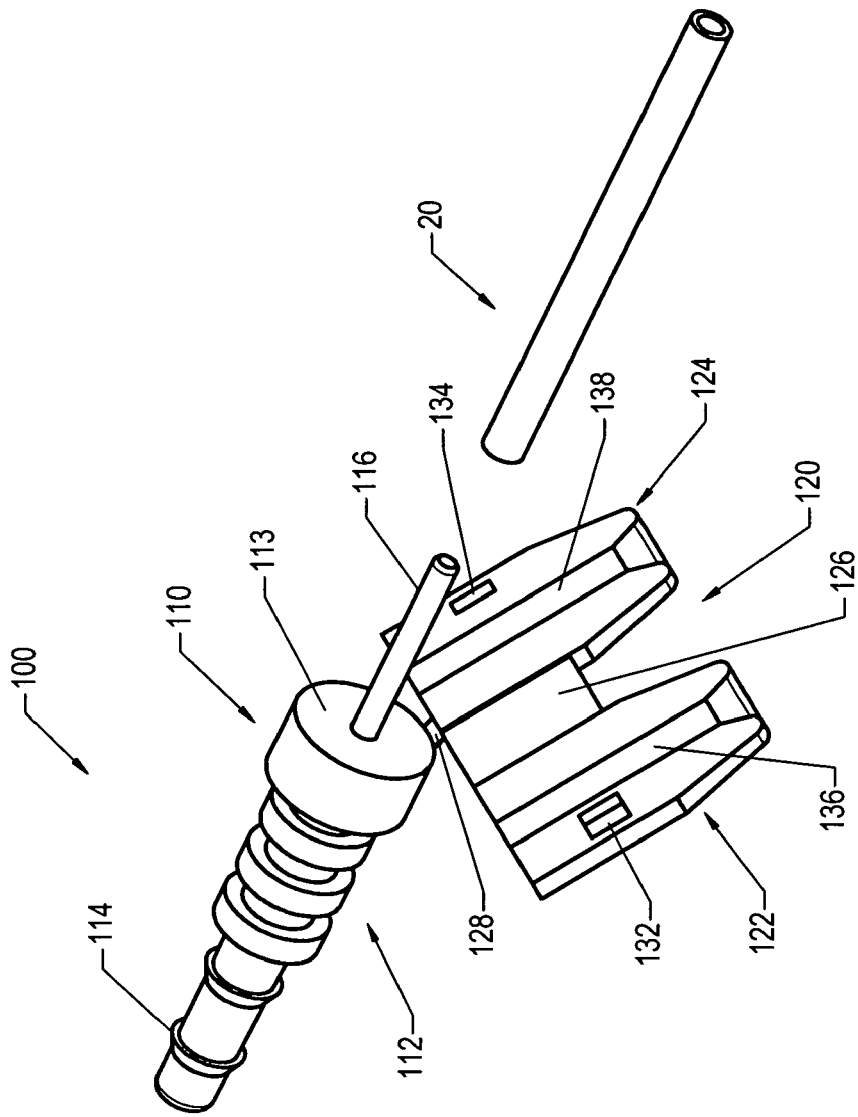
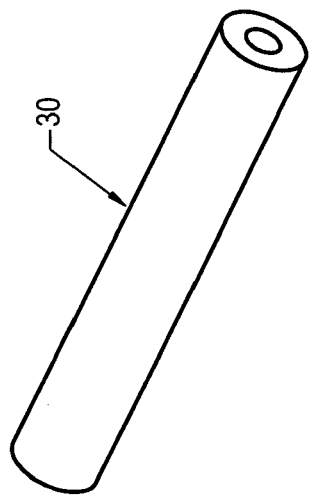
FIG 2

CATHETER CONNECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

It is common to use an implanted catheter to repeatedly access the vascular system of a patient and with the catheter perform repeated therapeutic medical activity. Such therapeutic activity could include the intermittent or continuous infusion of medication and fluids, the periodic sampling of blood, or the continuous withdrawal and return of blood for processing outside of the body of the patient. The catheters used in these activities are referred to as vascular access catheters.

Before any therapeutic activity can actually commence, however, the vascular access catheter must be implanted in the body of the patient with the distal tip of the catheter residing at the location in the vascular system at which an intended therapeutic activity is appropriate. Typically, most of the length of an implanted vascular access catheter resides within blood vessels of the vascular system, extending from the distal tip of the catheter to a location in the vascular system at which the catheter, by traversing a puncture or incision formed through a wall of the blood vessel in which the catheter is disposed, enters into the surrounding subcutaneous tissue of the patient. The location at which this occurs is referred to as a venipuncture site. Venipuncture sites are classified on the basis of the position of a venipuncture site in relation to the center of the body of the patient. Central venipuncture sites are those that enter the vasculature through the jugular or subclavian veins. Peripheral venipuncture sites typically enter the basilic or cephalic veins of the upper or lower arm. The freedom to select among venipuncture sites is determined largely on catheter size and vein size. Vein size is dependent on patient size and on location within the body, with peripheral veins being smaller than central veins.

Proximal of the venipuncture site, the implanted catheter extends through the subcutaneous tissue of the patient to emerge through the skin at a location that is referred to as the skin exit site. Most skin exit sites are chosen as being locations at which the proximal end of the implanted catheter can be easily manipulated by medical personnel. Favored among such locations are the neck, the region about the collar bone or chest wall, the upper leg, the upper arm, and the forearm. Occasionally, the skin exit site is somewhat removed from the venipuncture site. Then a significant portion of the length of the implanted catheter must be embedded in the subcutaneous tissue of the patient in a surgically created tunnel that extends from the venipuncture site to the skin exit site. In all instances, a portion of the proximal end of an implanted catheter must remain outside of the body of the patient. It is this portion of an implanted catheter, from the proximal end thereof to the skin access site, that is referred to as the extracorporeal portion of the implanted catheter.

The extracorporeal portion of an implanted catheter must be capable of being selectively coupled to and uncoupled from the tubing and medical equipment outside the body of the patient that are required for therapeutic activity. Accordingly, the proximal end of virtually all vascular access catheters terminates in a catheter coupling hub that can be secured in fluid communication with such tubing and medical equipment, or can be capped, valved, or clamped closed between periods of actual use. Due to the variation in length of catheter that is required to traverse the subcutaneous and intravascular route from implanted tip location to skin exit site, it often becomes necessary to trim the catheter to an appropriate length. Traditionally, it is the distal end of the catheter that is trimmed as opposed to the proximal end for a number of reasons, including the desire to provide accurate positioning of a pre-connected proximal suture wing hub in a desired location near the venipuncture site. In particular, clinicians are increasingly showing a preference for a stepped-taper or reverse-taper of the hub to be inserted partially into the venipuncture site to affect tamponade and reduce site bleeding.

Trimming the catheter to an appropriate length is particularly advantageous with respect to peripherally inserted central catheters (PICCs) where precise central venous catheter tip placement at the right atrial (RA), superior vena cava (SVC) junction is imperative to prevent potential thrombosis, traumatic or functional complications. Many types of catheters, however, cannot be distally trimmed due to the special configuration thereof, including, for example, dual lumen catheters with a pre-staggered tip, soft tip catheters, catheters with valved distal ends, etc. In the case of such catheters, a pre-connected hub at the proximal end of the catheter cannot be accurately located at the venipuncture site and, consequently, some length of catheter extends therefrom. This excess catheter length often presents difficulty in dressing the catheter and exposes the catheter to potential damage. Moreover, it is not possible in the placement of catheters having preformed distal tips to achieve tamponade at the venipuncture site.

Whether or not the catheter has a preformed distal tip, it is advantageous to be able to trim a catheter at its proximal end prior to connection to a coupling hub or other extracorporeal medical equipment because proximal trimming enables physicians to keep inventory low (as several different catheter lengths are unnecessary) and each catheter placed can be customized to the exact length optimal for patient comfort and operability of the catheter. As a result, many types of connection systems have been proposed to couple a proximal end of a catheter to a medical device.

With particular reference to a catheter that has been subcutaneously placed, in which an extracorporeal portion is to be connected to a coupling hub, systems such as that shown in FIG. 1 have been traditionally utilized. As shown, a catheter 20 is attached to a coupling hub 12 through three pre-assembled pieces. The proximal end of the catheter 20 is slid through strain relief sleeve 18, distal coupling 16 and compression sleeve 14. The proximal end of the catheter 20 is then slid over the cannula of coupling hub 12. Distal coupling 16 is snapped into coupling hub 12, exerting pressure against compression sleeve 14, which in turn retains catheter 20 on the cannula coupling hub 12. While such a connection system may be adequate for providing a secure connection, assembly can prove problematic due to the small size of the pieces involved as well as the extremely limited space with which the physician typically has to work. Moreover, the manufacture of several different pieces may lengthen the time to manufacture, as well as the cost associated therewith.

Connection systems for catheters that are not designed for proximal trimming, generally also require multiple separate pieces for assembly and consequently suffer the same drawbacks described above. Thus, it would be advantageous to provide a catheter connector or connection system for a single or multi-lumen catheter that would provide a secure connection to withstand standard pressures, while being easy to connect to the catheter, requiring little assembly and handling of parts by a physician.

Accordingly, it is the object of the present invention to provide a catheter connector, which safely and effectively connects a proximal end of a catheter to extracorporeal medical equipment, following placement of the distal end of the catheter in a patient. It is a further object of the present invention to provide a catheter connector for the connection of a single or multiple lumen catheter to extracorporeal medical equipment, utilizing very few parts so that ease of handling is facilitated and aligning problems are reduced, that is inexpensive and easy to manufacture, that securely connects the catheter to tubing or medical equipment while ensuring long-term patency of the catheter at the proximal connection point, and which can be attached and detached to and from the catheter quickly and efficiently. It is another object of the present invention to provide a connection system, including a catheter and bifurcation assembly, that may be quickly and securely assembled and which may be configured for permanent attachment or may be detachable.

Various other objectives and advantages of the present invention will become apparent to those skilled in the art as more detailed description is set forth below.

BRIEF SUMMARY OF THE INVENTION

The present invention is directed to catheter connector or connection system for a subcutaneously placed catheter. The catheter connector or connection system may be configured for a single lumen catheter or a multiple lumen catheter. The catheter connector or connection system facilitates precise positioning of both distal and proximal ends of a catheter, providing enhanced functionability and patient comfort.

In one embodiment, a catheter connector comprises a body comprising a cannula and a tail, said cannula extending from a distal end of said body and being sized to slidingly receive a catheter thereon, said tail extending from a proximal end of said body and being sized to slidingly receive a tube thereon, wherein said body is configured for fluid flow therethrough, and a securement device attached to said body at said distal end, comprising mating portions configured to secure said catheter to said body by locking together around said catheter following positioning of said catheter over said cannula.

In another embodiment, an assembly for connecting a catheter to extracorporeal medical equipment comprises a catheter connector comprising a body having a lumen therethrough and a securement device attached to said body at a distal end thereof, said securement device configured to secure said catheter to said body such that said body lumen is in fluid communication with said catheter, a tube connected at one end to a proximal end of said body and at an opposite end to a hub such that said body lumen is in fluid communication with said hub, and a covering positioned over at least a portion of said body and said tube, said covering being adapted for attachment to a patient.

In another embodiment, a catheter connector comprises a stem having at least one lumen extending longitudinally from a proximal end to a distal end, said stem comprising at least one prong positioned at said distal end, configured for insertion into a lumen of a catheter, at least one extension tube in fluid communication with said lumen of said stem, a hub surrounding at least a portion of said stem, configured for attachment to a patient, a clamp coupled to said stem, configured to close around a tip of said prong following insertion of said prong into said lumen of said catheter, and a collar being movable from a first position to a second position, wherein said collar in said second position retains said clamp in a closed position.

In yet another embodiment, an attachable bifurcation comprises a stem enclosing a first and second lumen and comprising a first and second prong at a distal end thereof, wherein said first and second prongs are configured for insertion into the proximal end of a dual lumen catheter, a first and second extension tube in respective fluid communication with said first and second lumens of said stem, a hub surrounding at least a portion of said stem, configured for attachment to a patient, a clamp coupled to said stem, configured to close around said first and second prongs following insertion of said prongs into said dual lumen catheter, and a collar movable from a first position to a second position, wherein said collar in said second position retains said clamp in a closed position.

In still another embodiment, a catheter connector for attachment to a catheter, wherein said catheter comprises at least one lumen and a hub attached to a proximal end thereof, comprises at least one cannula and a latching mechanism disposed near a proximal end of said cannula, said latching mechanism extending outwardly from a longitudinal axis of said cannula in a first position and being movable inward toward said longitudinal axis in a second position, said latching mechanism being biased in said first position.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 2 is a side view of a catheter connector according to the present invention in an open position.

DETAILED DESCRIPTION OF THE INVENTION

Figure 1:
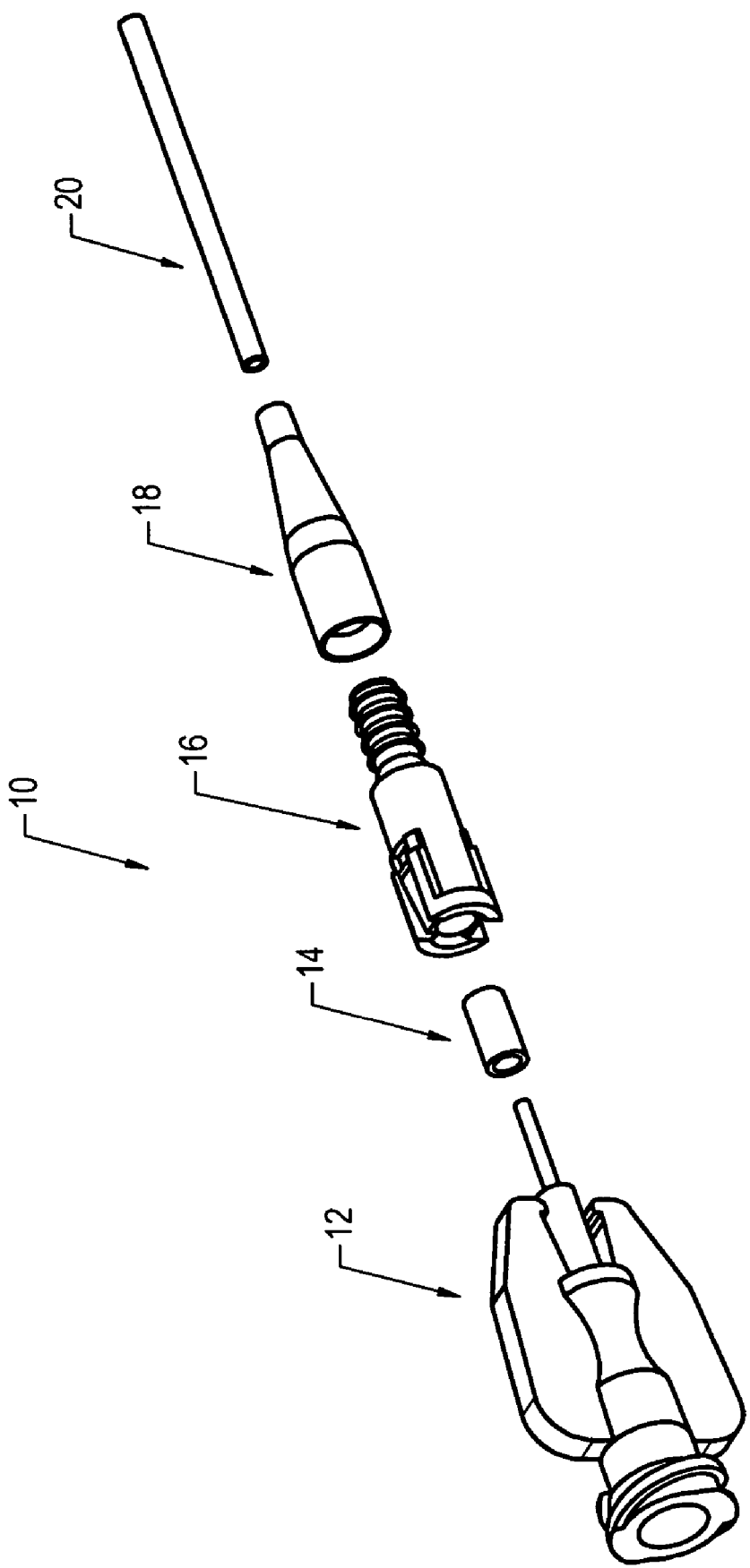
FIG. 1 is an exploded view of a prior art catheter connector system.

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention is directed to a catheter connector for connecting a catheter to extracorporeal medical equipment. In the embodiments and examples that follow, reference will be made to a catheter connector for a catheter that has been trimmed proximally, following placement thereof in the body of a patient. However, it should be understood that the present invention is not limited to such uses and instead is applicable to any application that requires the connection of a catheter to separate medical equipment as would be apparent to one of skill in the art. Moreover, when discussing the catheter connectors of the present invention in terms of attachment to a patient, it should be understood that attachment can be direct through suturing or other means, or indirect through the use of a StatLock® or other intermediary device. Also, the terms "cannula" and "stem" are used generically herein and should not be construed as being of any particular configuration or material.

Referring now to FIG. 2, one embodiment of a catheter connector according to the present invention is illustrated in a pre-connected, open position. Catheter connector 100 has a body 110 and a securement device 120 attached to the body 110 by a first living hinge 128. In this embodiment, the body 110 and the securement device 120 are unitary. As used herein, the term "unitary" refers to a design in which separate members or parts are manufactured in the same mold to form a one-piece unit. The body 110 at its proximal end has a tail 114, sized to receive a tube 30. In one embodiment, as shown, the tail 114 has a barbed end to assist in retention of the tube 30 once the tube 30 has been positioned over the tail 114. At the distal end of the body 110, a cannula 116 extends from a face 113 thereof, the cannula 116 being sized to slidingly receive a catheter 20. In one embodiment, the body 110 and the tail 114 are made of a hard plastic material, while the cannula 116 is made of metal. It should be understood, however, that the choice of materials is wide-ranging, and any suitable material as known to one of skill in the art would be equally within the scope of the present invention. The body 110 also contains a ribbed middle region, characterized by one or more grooves, which is an optional feature that can provide a securing function with respect to a winged covering apparatus positioned therearound (e.g., winged covering apparatus 60 (FIG. 5)).

Figure 3:
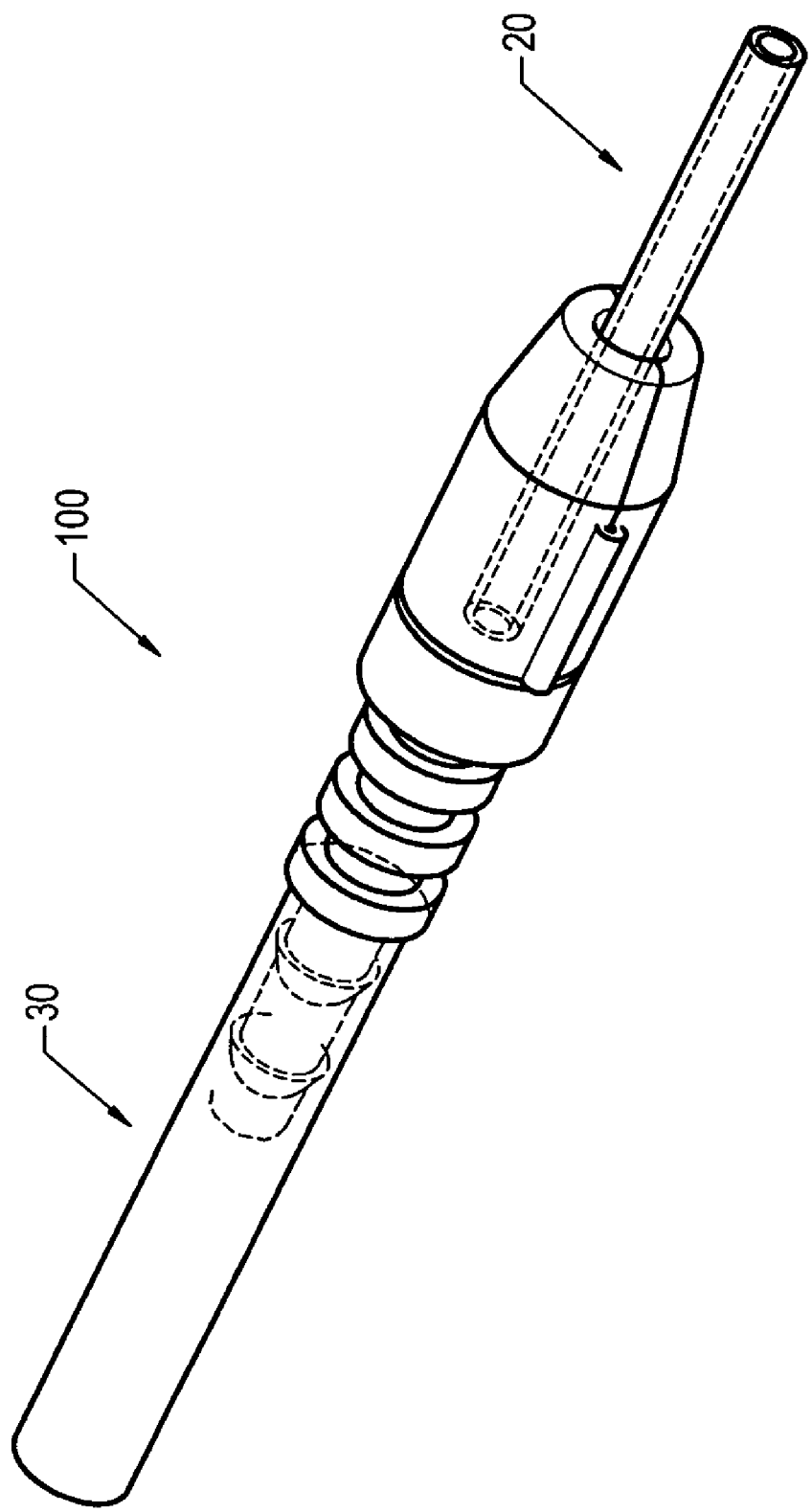
FIG. 3 is a side view of the catheter connector of FIG. 2 in a closed position.

Attached to the body 110 at face 113 is the securement device 120. As stated above, this attachment is accomplished via the first living hinge 128. The securement device 120 is shown in a shell-type configuration, having a first half 122 and a second half 124, which are essentially mirror images of one another. The first and second halves 122, 124 of the securement device 120 are connected by a second living hinge 126, each having a recessed mid-section 136, 138 respectively for reception of the cannula 116 and catheter 20 when the securement device is closed therearound in a closed position (FIG. 3). The first half 122 has an outwardly extending tab 132 for locking connection with a recess 134 on the second half 124 when the securement device 120 is in the closed position. It should be appreciated that although shown with a tab/aperture connection arrangement in FIG. 1, the securement device of the present invention could have many different types of locking arrangements as are known in the art. Moreover, the locking arrangements for the securement device 120 can be releasable or permanent. Further, as with all embodiments described herein, cannula 116 may include barbs or ribs positioned along its length to further ensure securement of the catheter thereon. In such an arrangement, mid-sections 136, 138 could be fashioned with cooperating recessed portions to receive the barbs or ribs. Another potential gripping aid would be discontinuous surfaces on mid-sections 136, 138.

FIG. 3 illustrates the catheter connector 100 in a closed position, with tube 30 and catheter 20 connected to the body 110. In practice, following placement of the distal end of the catheter 20 into a patient, the proximal end thereof may be trimmed to the desired length, if necessary. The physician slides the catheter 20 over the cannula 116, presses the second half 124 of the securement device 120 upward such that the portion of the catheter 20 slid over the cannula 116 is snugly received in mid-sections 136, 138, and finally swings the first half 122 of the securement device 120 over the opposite side of the catheter/cannula coaxial arrangement and into locking arrangement as tab 132 is received into recess 134. The entire portion of the catheter 20 that has been slid over the cannula 116 is thus covered by the securement device 120, being received into mid-sections 136, 138 thereof. It should be noted that the mid-sections 136, 138 are dimensioned such that upon closing around the catheter/cannula coaxial arrangement, the securement device 120 tightly presses the catheter 20 against the cannula 116, whereby normal pulling forces will not remove the catheter 20 from the securement device 120.

Figure 4:
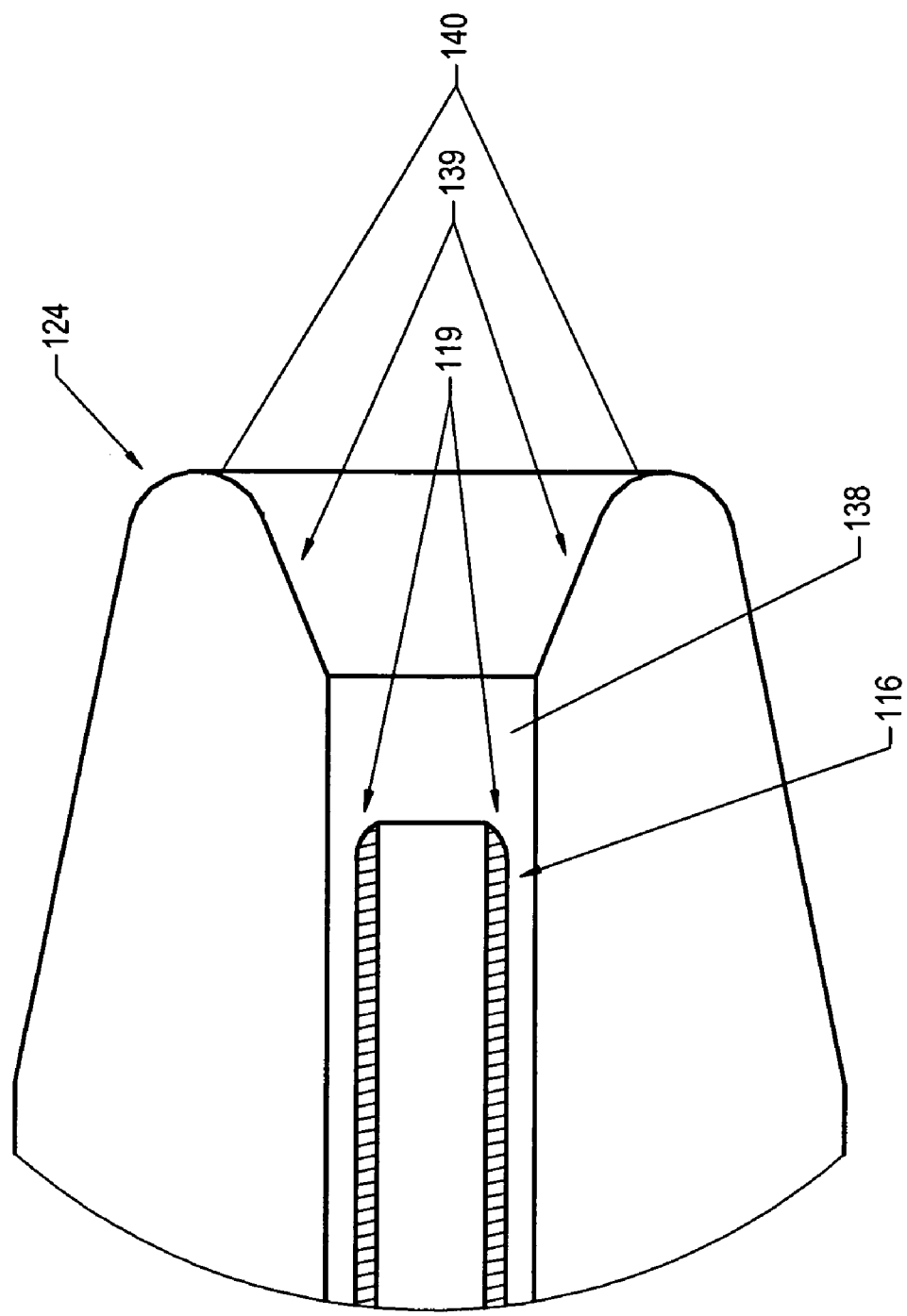
FIG. 4 is an enlarged view of an embodiment for a distal end of a catheter connector according to the present invention.

Referring to FIG. 4, optional features of the catheter connector 100 to prolong the patency of the catheter 20 are illustrated. FIG. 4 shows a partial top enlarged view of the second half 124 of the securement device 120 in combination with a cross-sectional view of the cannula 116. With respect to the cannula 116, an edge 119 thereof is rounded, beveled or otherwise blunted to reduce the possibility of catheter damage. With respect to the securement device 120, the distal ends of one or both of the first and second halves 122, 124 are configured to funnel away from the cannula 116 in a closed position, thus providing both strain relief and kink prevention for a catheter 20 that may be pulled to one side or another of the securement device 120. FIG. 4 illustrates this aspect, showing funneled sides 139 extending outwardly from mid section 138. In addition, rounded edges 140 provide further strain relief and kink resistance for a catheter that is bent around the edge of the securement device 120.

Figure 5:
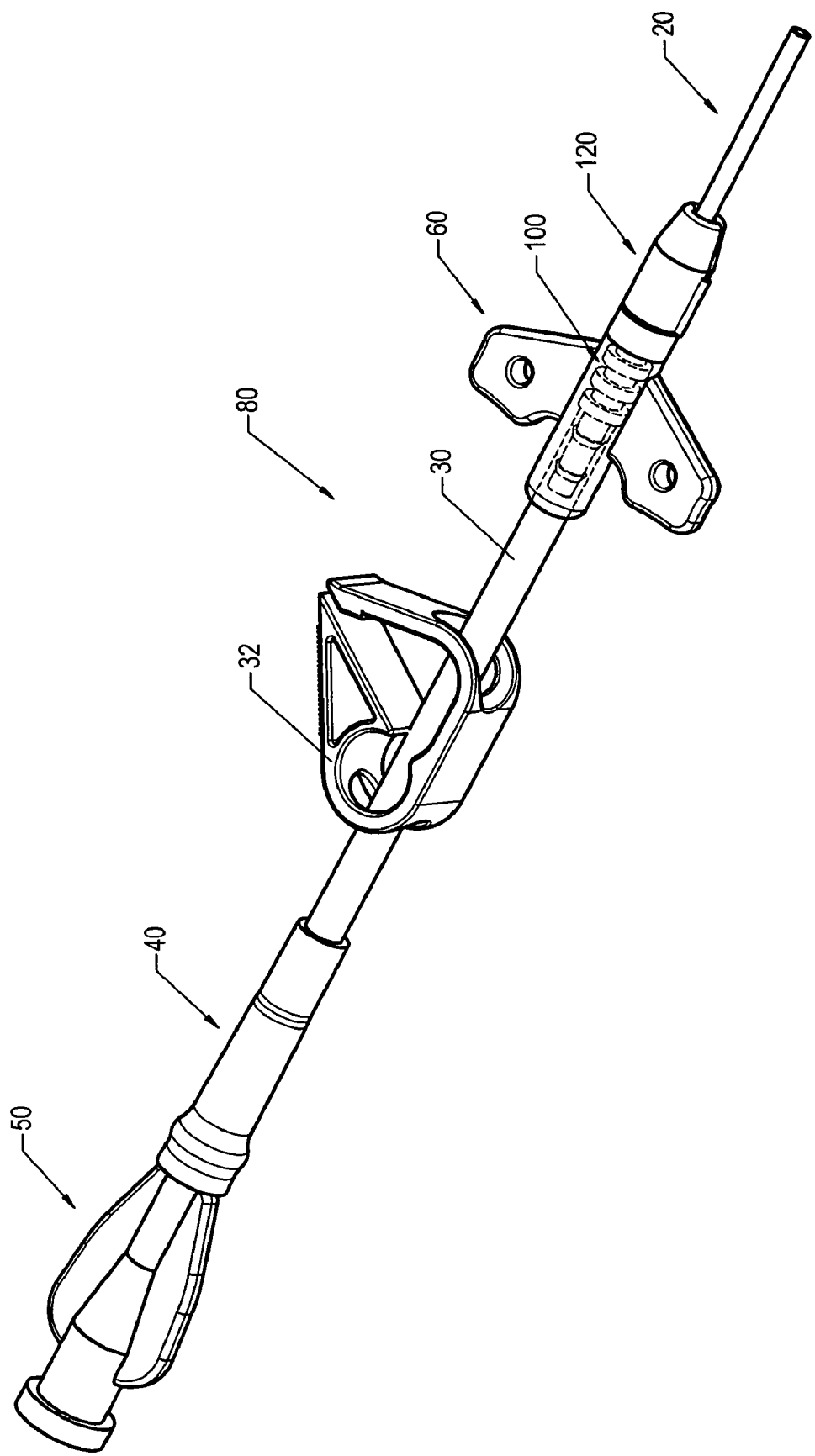
FIG. 5 is a top view of an assembled proximal end of a catheter connector system, including the catheter connector of FIG. 2.

FIG. 5 illustrates a connector assembly 80, incorporating the catheter connector 100, which is shown partially in phantom. The catheter connector 100 is in its closed configuration, connected to tube 30 and catheter 20, as shown in FIG. 3. Catheter connector 100 is largely enveloped by a winged covering apparatus 60, which is utilized to secure the catheter connector to the patient. As mentioned above, the ribbed region 112 of the body 110 of catheter connector 100 is configured to mesh with a corresponding region fashioned on the inner surface of winged covering apparatus 60. Thus, the matching ribbed regions prevent movement of the catheter connector 100 with respect to the winged covering apparatus 60 when assembled. One way to accomplish such a corresponding ribbed region on the inner surface of the winged covering apparatus 60 is to overmold the winged covering apparatus 60 around the catheter connector 100 such that the material thereof flows into the ribbed region of the catheter connector. Of course, one of skill in the art will appreciate that many types of textures other than ribbing, such as dimpling, could equally serve the desired goals of preventing relative movement of the catheter connector 100 and the winged covering apparatus 60. The winged covering apparatus 60 can be made of silicone or a like material to facilitate such a procedure, although certainly, various other materials would also be possible for apparatus 60. Extending from the distal end of the winged covering apparatus 60 is the securement device 120, such that the catheter 20 can be disconnected from the catheter connector 100 without removal of the apparatus 60. Proximal of the apparatus 60 is a hub 50 for selective connection to medical equipment, the hub 50 being secured to the tube 30 via securement sleeve 40 as is known to one of skill in the art. Positioned on the tube 30 is an optional clamp 32, used for selectively closing tube 30 to fluid flow.

The assembly 80 may be pre-assembled prior to shipping to facilitate use by a clinician in connecting catheter 20 to extracorporeal medical equipment. The order of assembly can vary, but in one embodiment, the tube 30 is first attached to hub 50 at a proximal end thereof and is secured thereto by sleeve 40. The distal end of the tube 30 is then attached to catheter connector 100, after which winged covering apparatus 60 is molded over portions of both the tube 30 and catheter connector 100, thereby permanently affixing one to the other. The assembly 80 is thus presented to the clinician as a unitary device.

Figure 6:
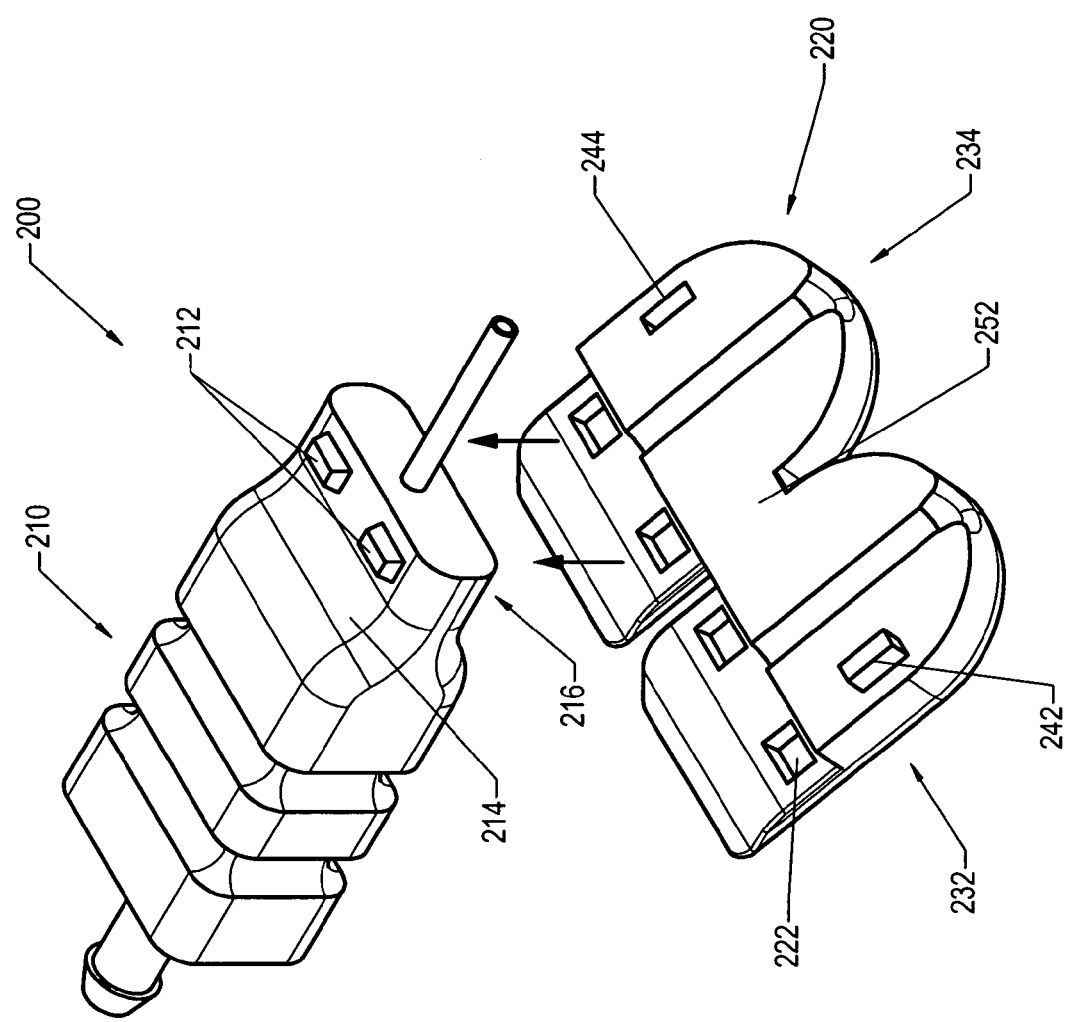
FIG. 6 is a side view of another embodiment of a catheter connector according to the present invention in a pre-assembled open position.
Figure 7:
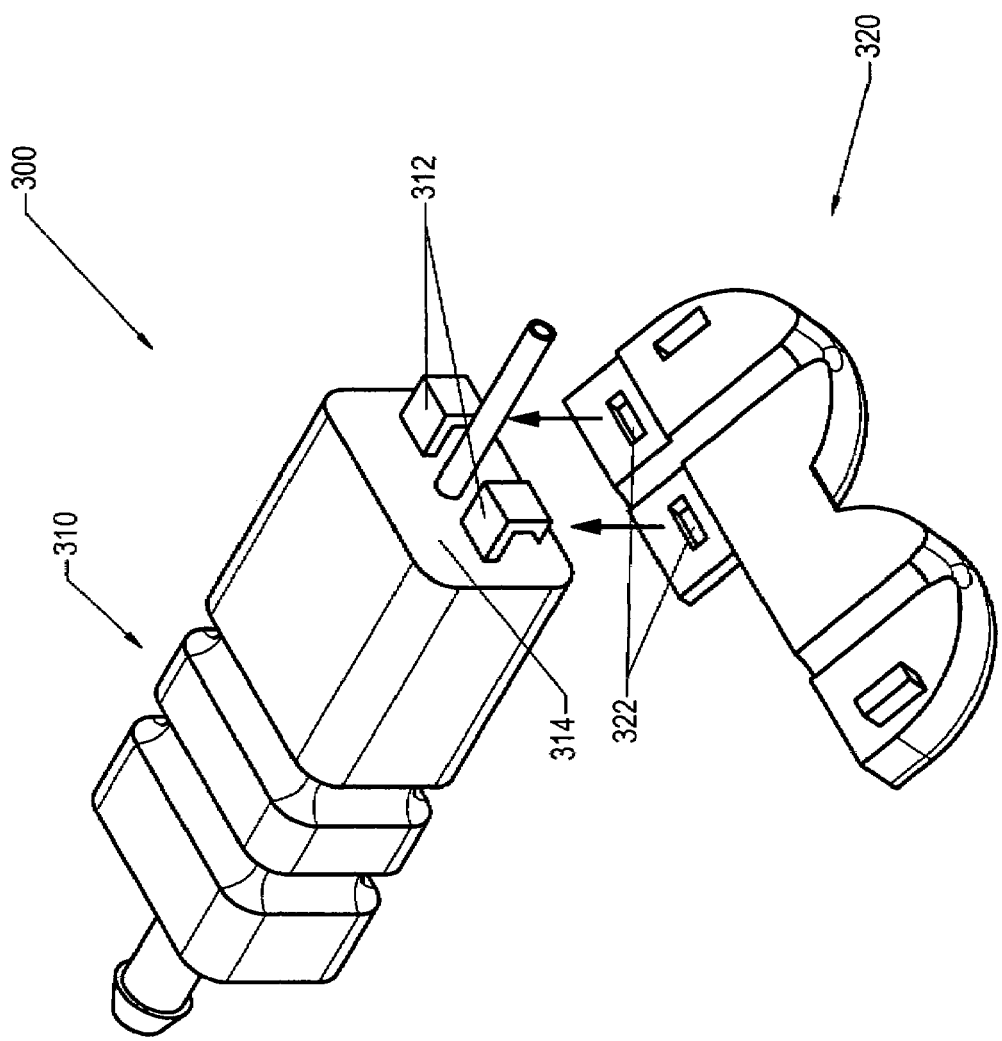
FIG. 7 is a side view of yet another embodiment of a catheter connector according to the present invention in a pre-assembled open position.

FIG. 6 illustrates a catheter connector 200, which is another embodiment of the present invention. In this embodiment, a securement device 220 is manufactured separately from a body 210, the two of which are connected prior to use. The connection mechanism employed is a tab/recess arrangement in which tabs 212 that are positioned on both a top face 214 and a bottom face 216 of body 210 are configured to be received into recesses 222 positioned on the securement device 220. Securement device 220 has mating halves 232, 234 separated by a living hinge 252. Similar to the securement device 120 described above, securement device 220 contains a tab 242 on a first half 232 that is received into a recess 244 on a second half 234 when the securement device 220 is in a locked position around a catheter. Referring to FIG. 7, another embodiment of the present invention is shown, in which catheter connector 300 contains a slightly different connection mechanism with respect to a body 310 and a securement device 320. In this embodiment, a face 314 of the body 310 has hinges 312 attached thereto, the hinges 312 configured for locking reception into recesses 322 in securement device 320. Of course, it should be appreciated that many different types of connection mechanisms are possible in embodiments that have a body and securement device initially separated, which would equally be within the scope of the present invention.

Figure 8:
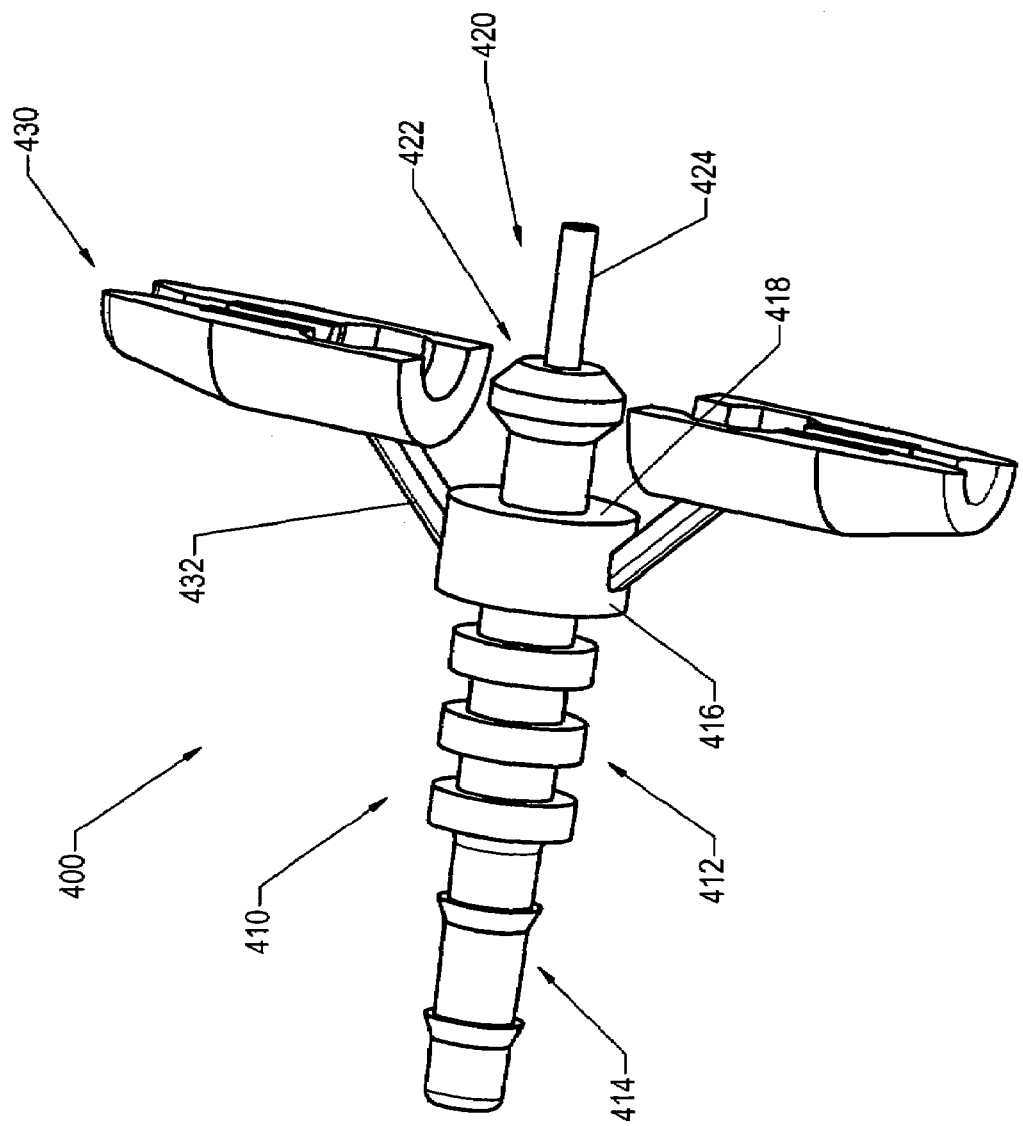
FIG. 8 is a top view of still another embodiment of a catheter connector according to the present invention in an open position.
Figure 9:
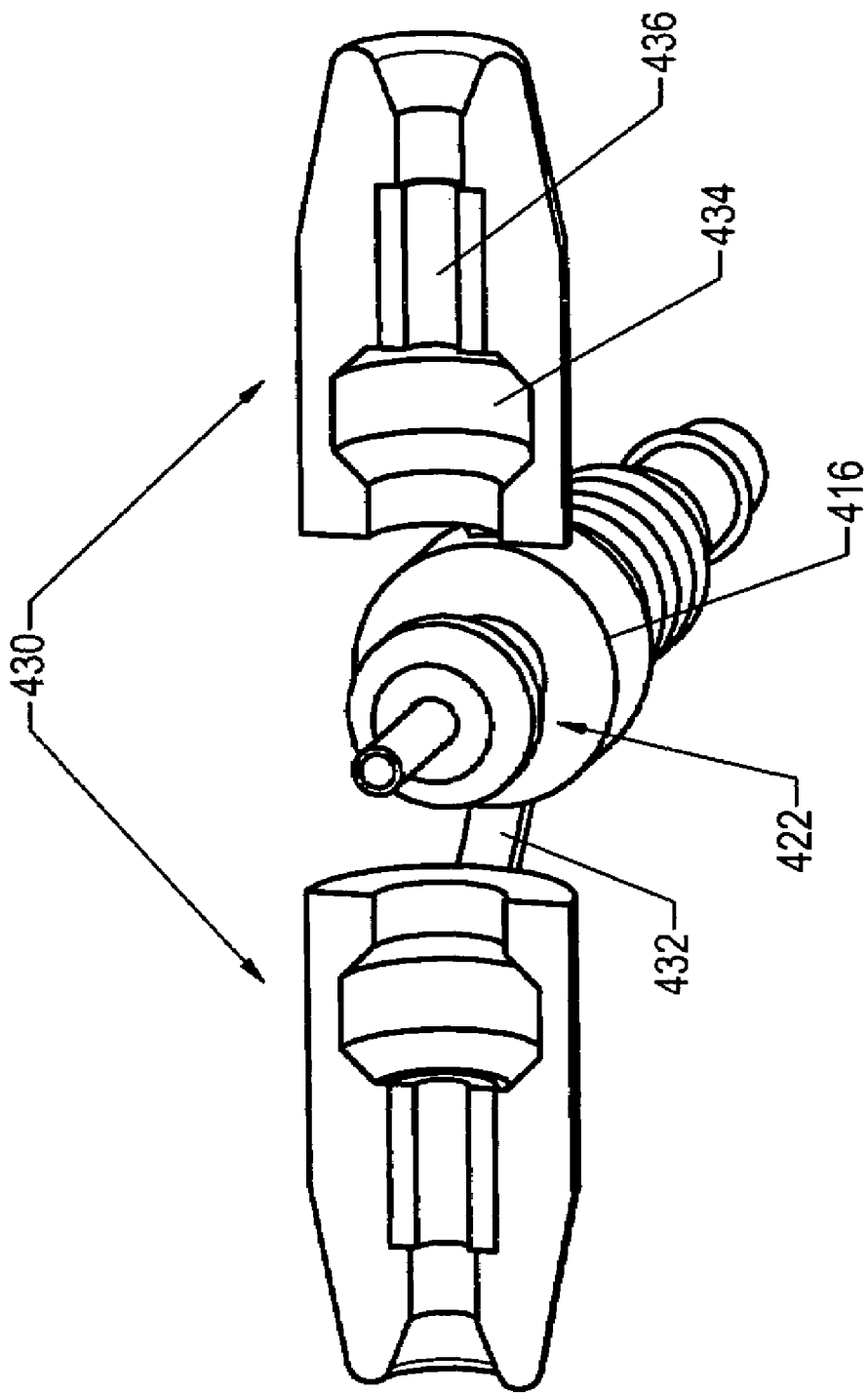
FIG. 9 is a front view of the catheter connector of FIG. 8.

FIG. 8 illustrates another embodiment of the present invention. From a top view, catheter connector 400 can be seen, having a body 410, which includes a ribbed middle region 412, a tail 414 and a front portion 416. Attached to opposite sides of the front portion 416 are arms 432 that each carry a mating half of a securement device 430. Extending from a face 418 of the front portion 416 is a head 422 from which extends a cannula 424. FIG. 9 shows a front view of the catheter connector 400, in which the inside of the securement device 430 can be seen. Each half of securement device 430 contains a cut-away portion 434, configured to receive the head 422 when the catheter connector 400 is placed in a closed position. The cut-away portion 434 is sized larger than the head 422 so that when the securement device 430 is closed therearound, the head 422 is surrounded by the securement device 430, thereby attaching the securement device 430 to the body 410 in the event that the arms 432 should crack or break. This configuration permits the arms 432, instead of being constructed of the same material as the body 410 and securement device 430, to be made of a more rigid material or to have a thinner profile without compromising the integrity of the connection. The locking mechanism utilized to lock the securement device 430 can be the any of those described above or equivalent locking mechanisms known in the art. Each half of the securement device 430 also contains a liner 436 that is fashioned to tightly grip a catheter in the closed position.

Figure 10:
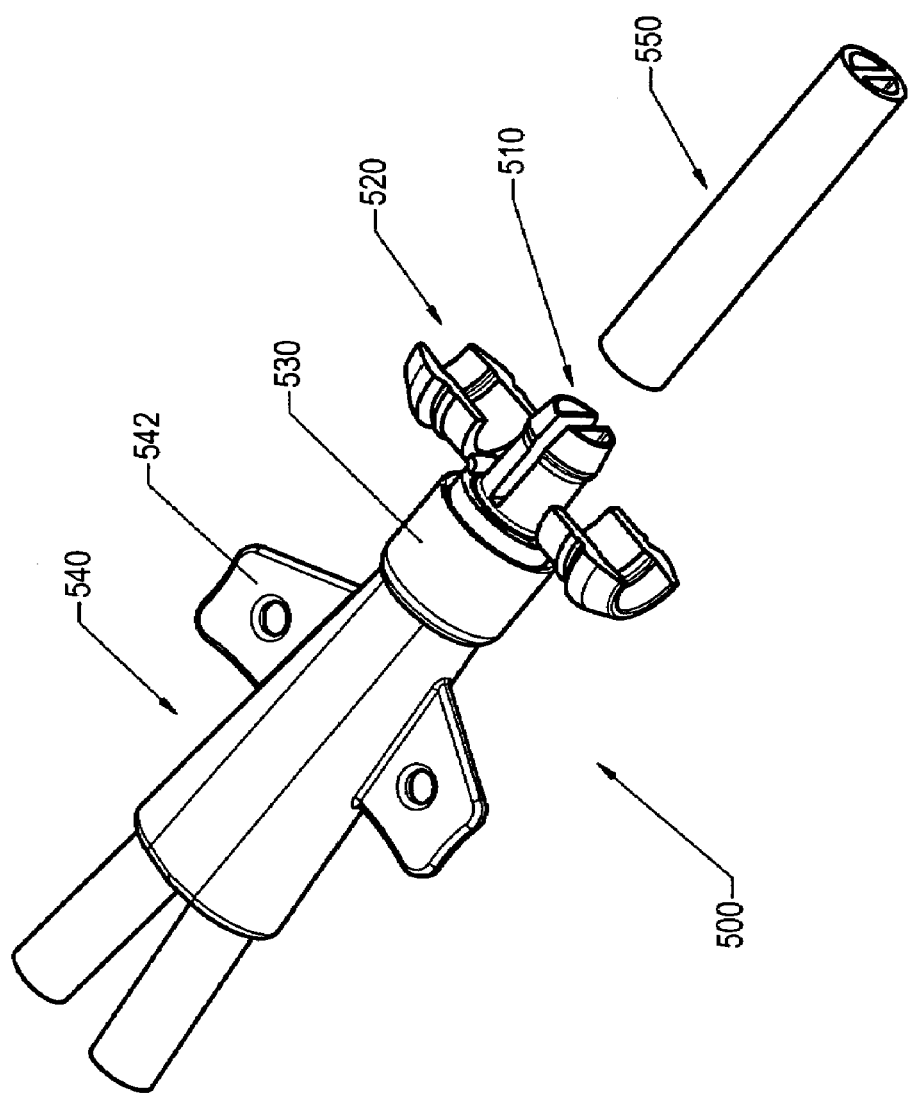
FIG. 10 is a perspective view of a catheter connector according to the present invention in an open position prior to attachment to a catheter.
Figure 11:
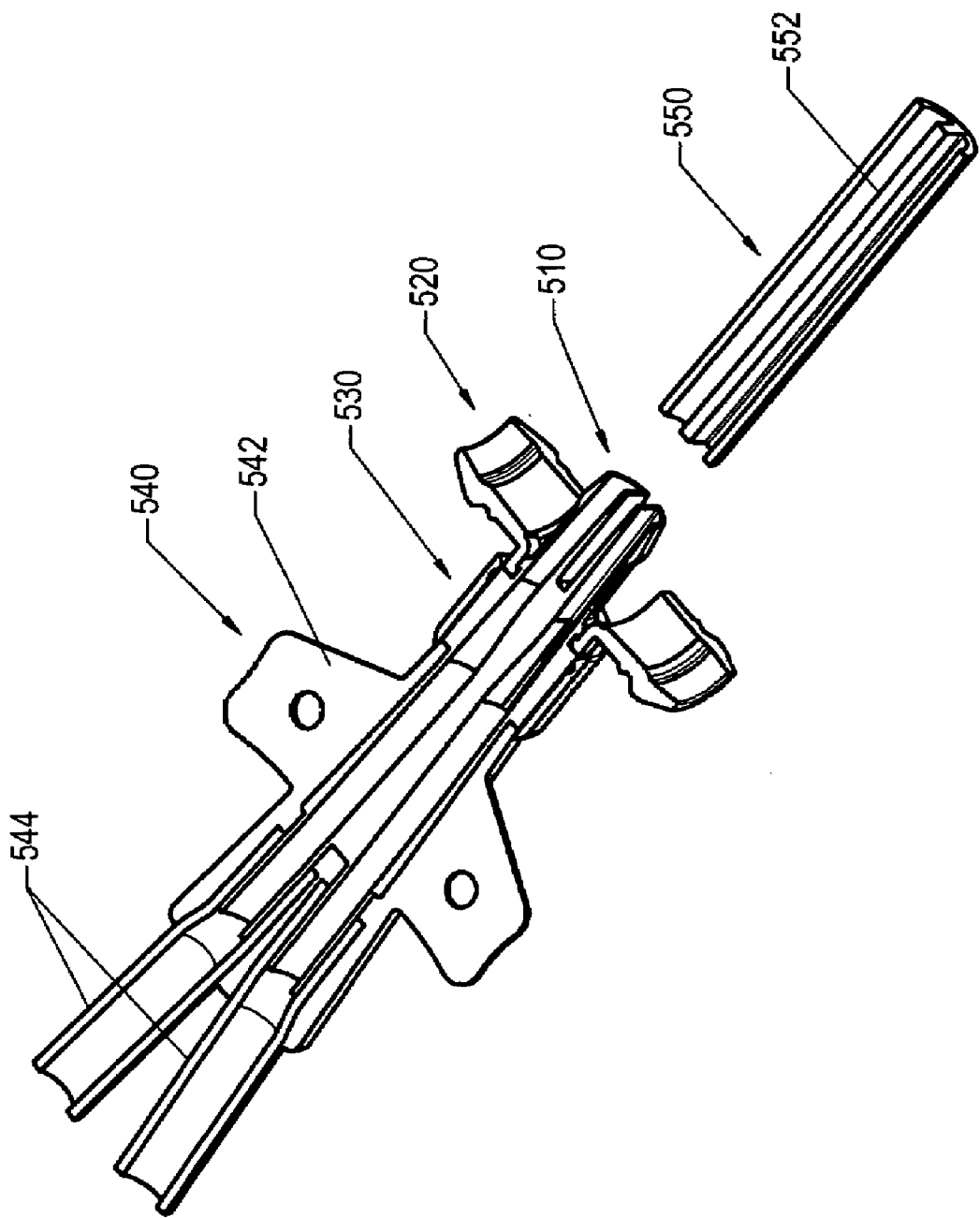
FIG. 11 is a longitudinal cross-sectional view of the catheter connector and catheter of FIG. 10.

In another embodiment of the catheter connector according to the present invention, catheter connector 500 is shown in FIGS. 10-15. FIG. 10 illustrates the catheter connector 500 prior to connection to a catheter 550. Catheter connector 500 consists primarily of a stem 510, a clamp 520, a collar 530 and a hub 540. Although catheter connector 500 is illustrated in a dual lumen configuration (i.e., as an attachable bifurcation), it should be appreciated that the design would be equally applicable for attachment to a single lumen catheter or a catheter having more than two lumens. FIG. 11 is a longitudinal cross-sectional view of the catheter connector 500, showing each of the component parts. As with the catheter connector 100, described above, catheter connector 500 can be attached to a catheter following placement thereof in the body of a patient and having been trimmed to an appropriate length.

Figure 12:
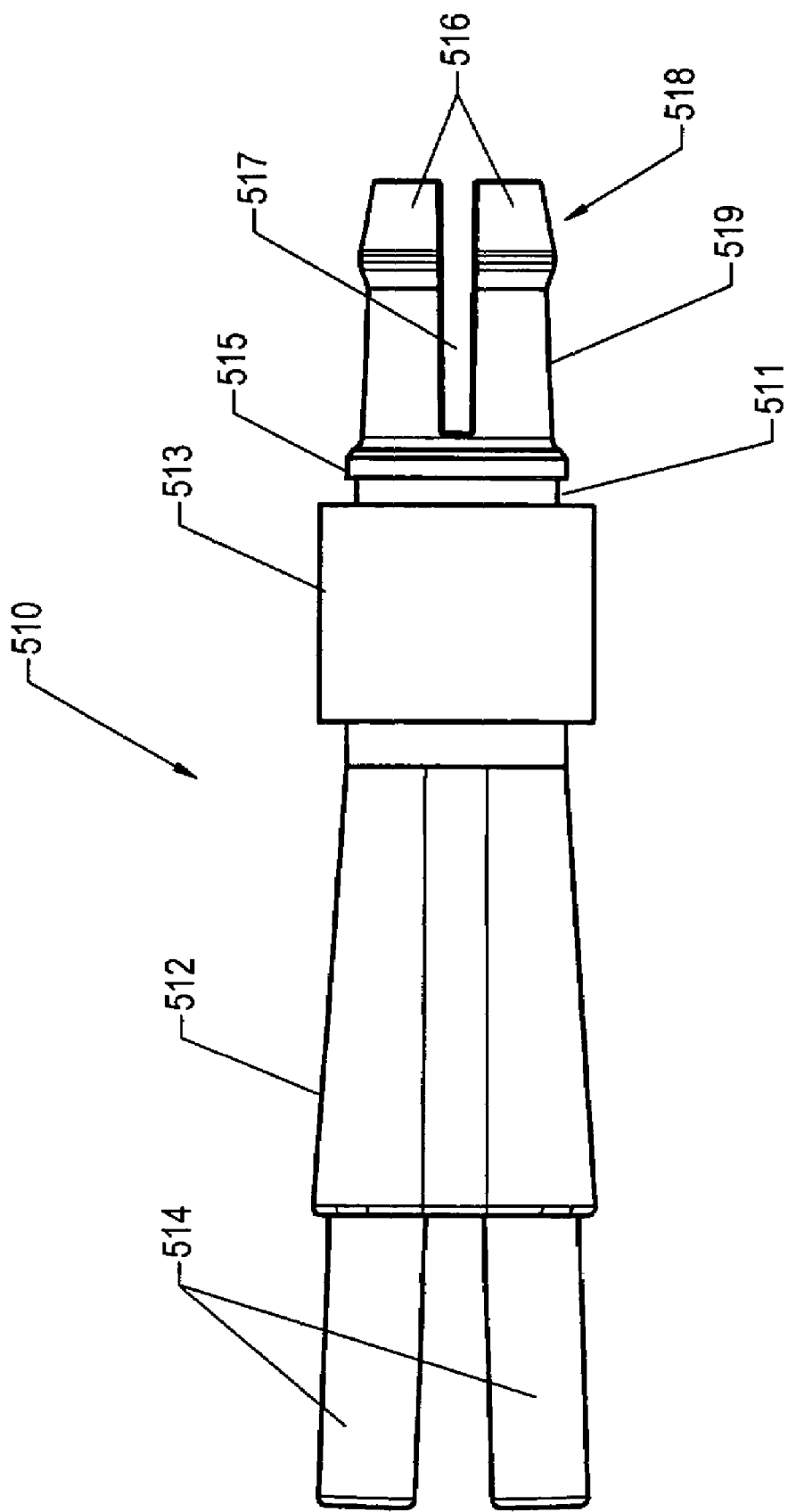
FIG. 12 is an isolated top view of the stem part of the catheter connector of FIG. 10.

FIG. 12 is an isolated view of the stem 510, showing a body 512, legs 514, a mid-portion 513 and dual prongs 516. As shown in FIG. 11, the stem 510 encloses two lumens that extend the entire length thereof to provide a fluid connection between the catheter 550 and extension tubing 544. The body 512 and legs 514 are covered by the hub 540, which can be molded over the stem 510 or attached by other means known to one of skill in the art. Referring back to FIG. 12, the mid-portion 513 has a diameter larger than the body 512, providing a shoulder for abutment of the hub 540, which results in a smooth outer surface for the catheter connector 500. The dual prongs 516 are configured for insertion into the dual lumen catheter 550, the gap 517 separating the prongs 516 being configured to match the thickness of the septum 552 of the catheter 550. In one embodiment the gap 517 is tapered to enhance the gripping of the septum 552. The prongs 516 each have a tip 518 that tapers distally from a larger diameter portion to a smaller diameter portion at an end thereof, as well as a neck 519 proximal the tip 518. The larger diameter portion of the tip 518 is preferably larger than the lumen of the catheter in which it is to be placed in order to stretch the lumen slightly and thereby prevent relative movement of the catheter with respect to the tip 518 after being placed thereover. Adjacent the neck 519 is a raised diameter portion 515, which acts as a stop to prevent further movement of the catheter 550 when the catheter 550 is slid onto the prongs 516. Positioned between the mid-portion 513 and raised diameter portion 515 is a recessed section 511, where the clamp 520 is anchored to the stem 510.

Figure 13:
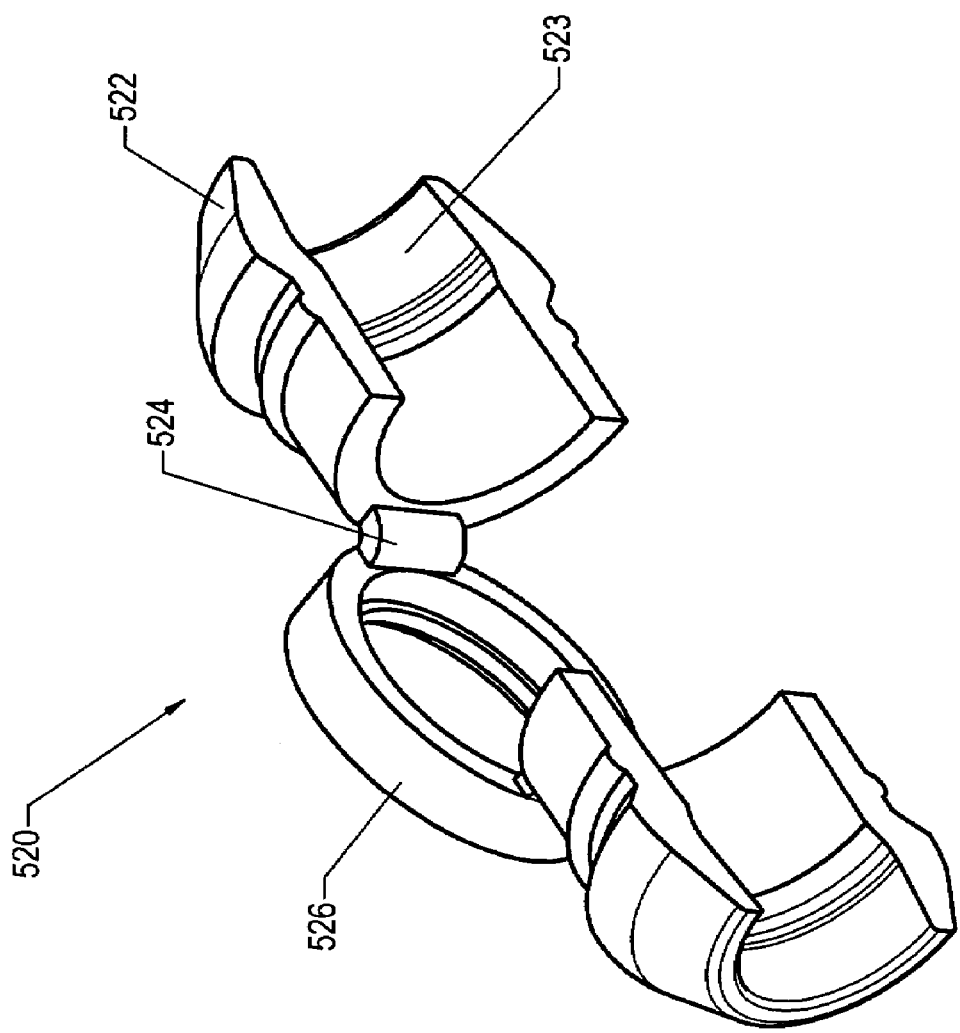
FIG. 13 is an isolated perspective view of the clamp part of the catheter connector of FIG. 10.
Figure 14:
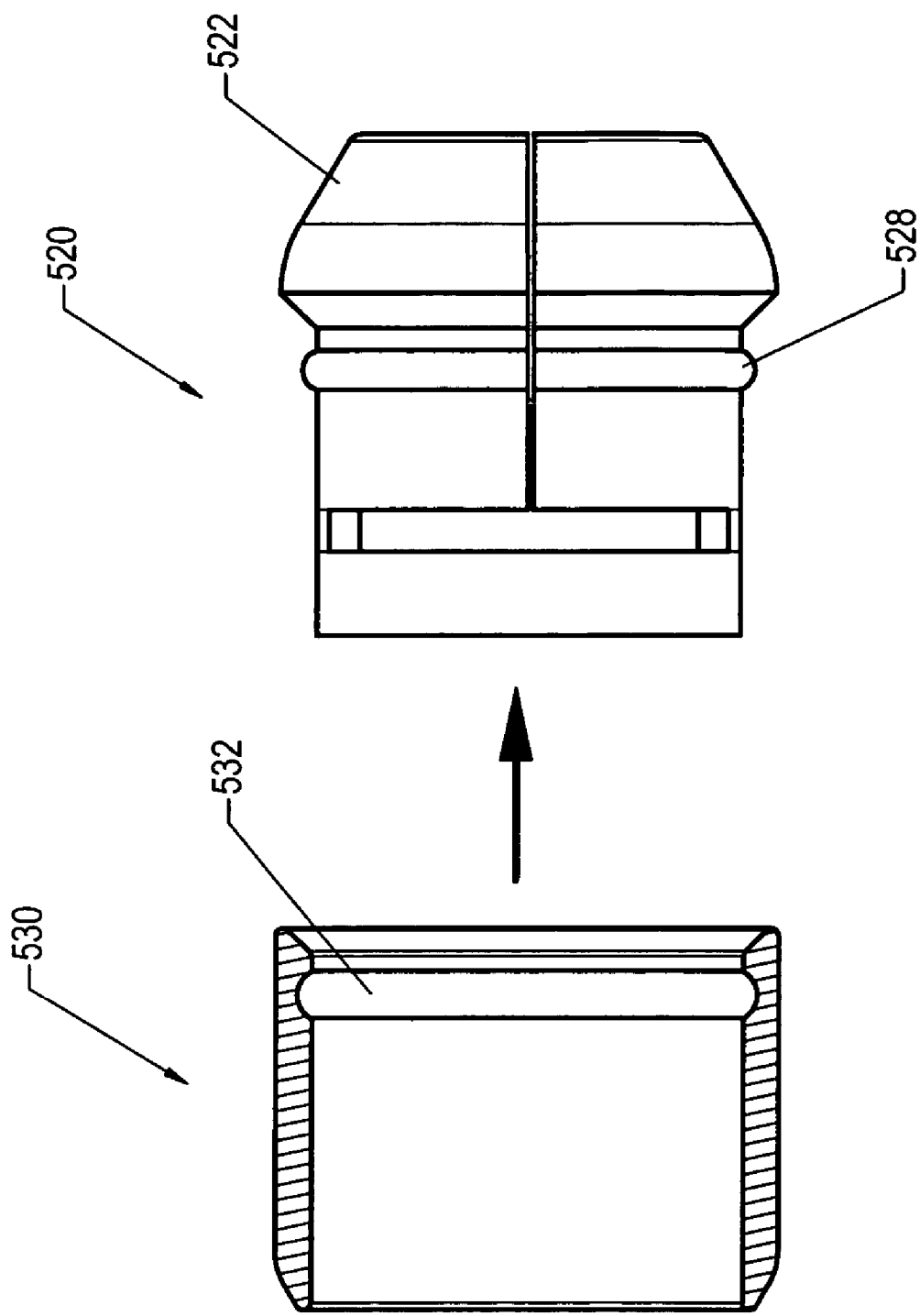
FIG. 14 is an isolated view of the clamp part of FIG. 13 in a closed position and a cross-sectional view of the collar part of the catheter connector of FIG. 10.

FIG. 13 illustrates in isolation the clamp 520, which includes a base 526 and matching members 522, each of which are attached to the base 526 via a living hinge 524. The members 522 are shell-shaped, each having a recessed inner surface 523 configured to tightly surround the tips 518 of the prongs 516 when pressed together. The base 526 is in the shape of a ring and is sized to fit within the recessed section 511 of the stem 510. FIG. 14 shows clamp 520 in its closed position and collar 530 in cross-section to illustrate the interconnection therebetween. More particularly, once the members 522 are pressed together, collar 530 is slid over the clamp 520 until the groove 532 on the inner surface of the collar 530 snaps over the top of raised section 528 on the outer surface of the clamp 520 to prevent the members 522 from opening inadvertently. To further prevent opening of the members 522, the clamp 520 and/or collar 530 may contain a latching mechanism. In one embodiment, the outer surface of the clamp 520 contains threads and the inner surface of the collar 530 contains mating grooves (or vice versa) such that instead of sliding, the collar is screwed onto the clamp 520.

Figure 15:
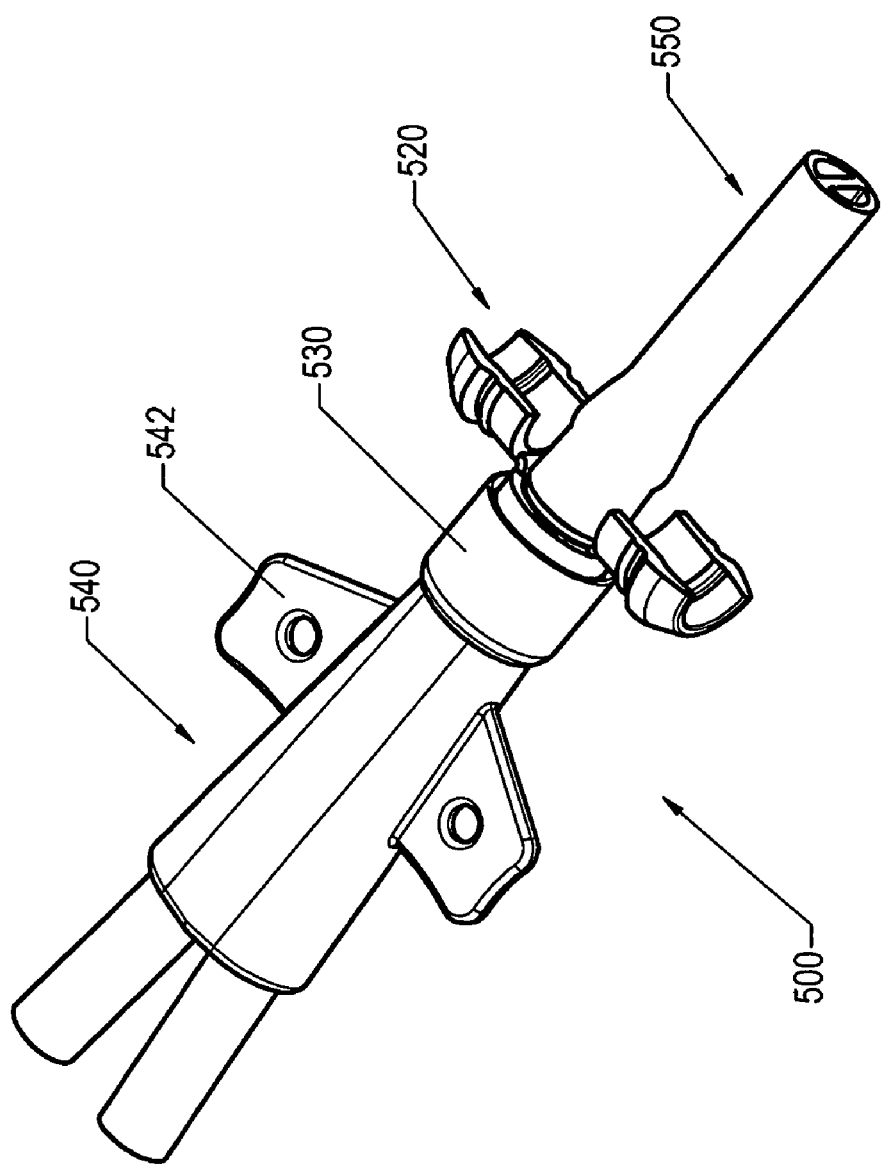
FIG. 15 is a perspective view of the catheter connector of FIG. 10 with the catheter being pushed onto the stem.
Figure 16:
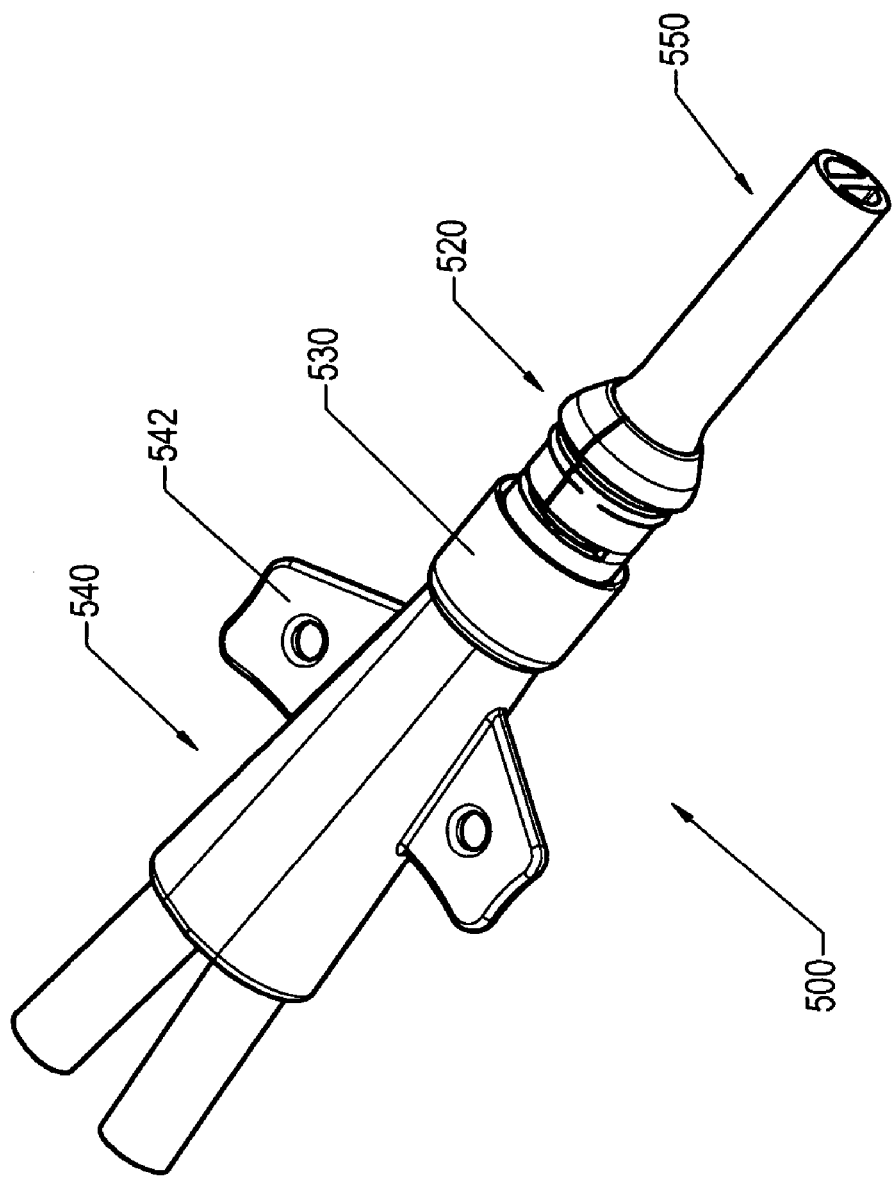
FIG. 16 is a perspective view of the catheter connector of FIG. 15 with the clamp closed around the catheter.
Figure 17:
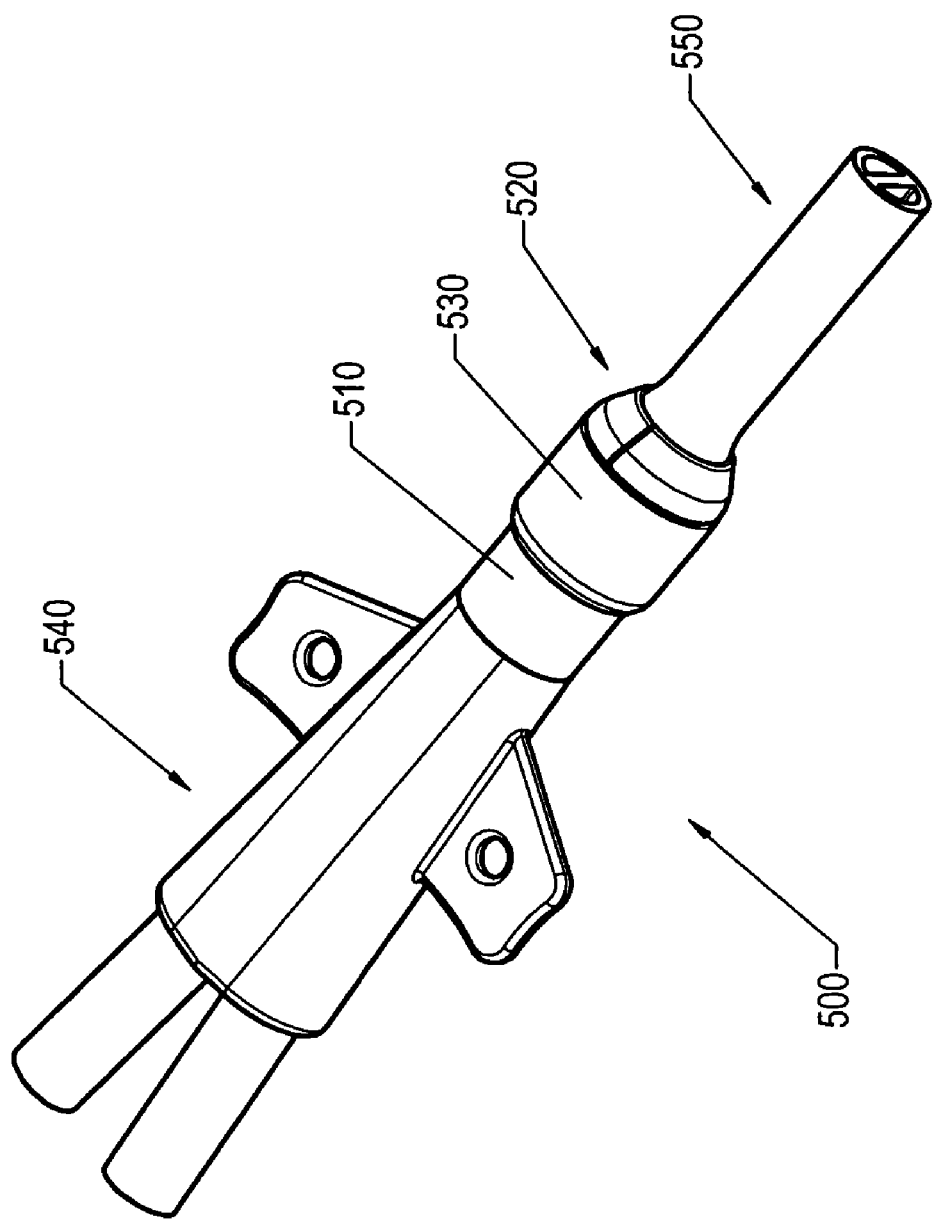
FIG. 17 is a perspective view of the catheter connector of FIG. 16 with the collar positioned over the closed clamp.

Referring back to FIG. 10, the catheter connector 500 is shown prior to attachment to a catheter, with the clamp 520 in an open position. FIG. 15 illustrates the first step in attaching the catheter 550 to the catheter connector 500 as the catheter is pushed onto the stem 510 as the prongs 516 are respectively slid into the lumens of the catheter 550. The catheter 550 is pushed in a proximal direction until further movement is prevented by raised portion 515. At this point, the catheter 550 is secured to the stem 510 due to the configuration of the tip 518, as explained above. The next step is shown in FIG. 16 as the members 522 are closed around the outer wall of the catheter 550 and tips of the prongs 516 therein. Finally, as shown in FIG. 17, the collar 530 is slid down from its position over the mid-portion 513 of stem 510, over the clamp 520 where it is snap-fit into position. As stated above, further means of attachment of the collar 530 to the clamp 520 are contemplated and would be within the scope of the present invention.

Figure 18:
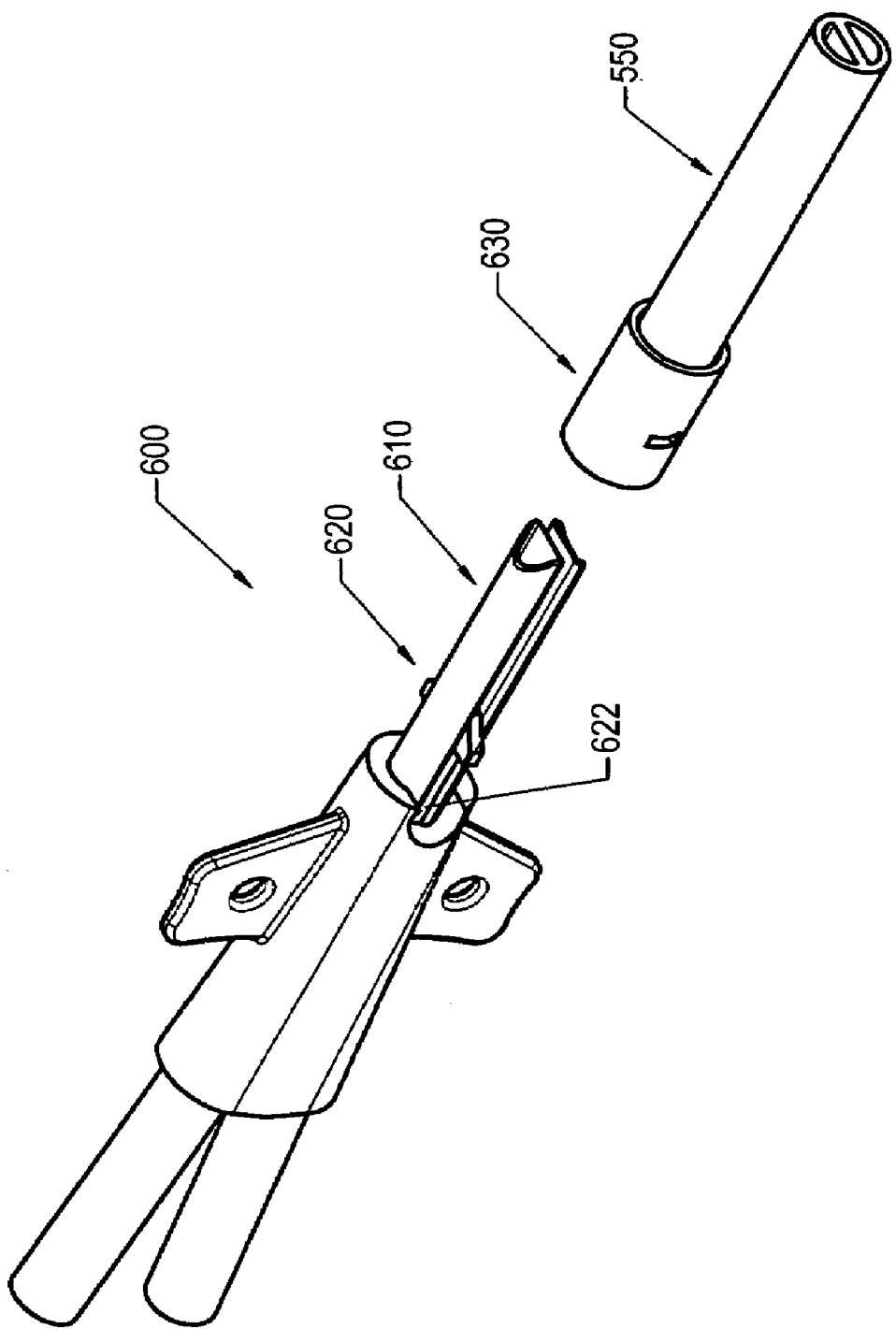
FIG. 18 is a perspective view of a catheter connector and catheter assembly according to the present invention.

FIG. 18 illustrates another embodiment of the present invention, in which catheter connector 600 employs a different attachment mechanism to catheter 550. In this embodiment, the catheter 550 has connected to its proximal end a hub 630 having internal indents for receiving latching mechanism 620 disposed on the catheter connector 600. The catheter connector 600, illustrated in a dual lumen configuration as an attachable bifurcation (but, again, could be in a single or multi-lumen configuration), has two cannulas 610 that are D-shaped in cross-section to match the D-shape lumens of catheter 550. Attached between the cannulas 610 (which may be made of stainless steel) toward the proximal end thereof is the latching mechanism 620 (which also may be made of stainless steel). The latching mechanism 620 has a wing-shaped configuration with an open and closed position, the open position shown in FIG. 18 and the closed position such that it lays flush with the outer diameter of the cannulas. The latching mechanism 620 is biased through spring action or the like to the open position, but can easily move to the closed position upon being pressed inward toward the longitudinal axis of the cannulas 610.

To attach the catheter connector 600 to the catheter 550, the cannulas 610 are aligned with the lumens of the catheter 550 and are slid therein through the hub 630. As the latching mechanism 620 comes into contact with the proximal end of the hub, it is pressed inward until reaching the internal indents of the hub, at which time the latching mechanism 620 springs outward to fill the space provided thereby, providing to the physician an audible snapping sound and tactile feel to confirm connection. Due to the configuration of the latching mechanism 620, the catheter connector 600 cannot be separated from the catheter 550 once filling the void provided by the internal indents of the hub, regardless of the possible pulling forces that could be applied in the course of standard usage. However, the catheter connector 600 may be disengaged by utilizing a tool that applies inward force to the proximal end 622 of the latching mechanism 620, whereby the outward extending portions of the latching mechanism fold inward, allowing easy removal of the catheter connector 600 from the catheter 550.

The present invention has been described above in terms of certain preferred embodiments so that an understanding of the present invention can be conveyed. However, there are many alternative arrangements for a catheter connector not specifically described herein, but with which the present invention is applicable. Although specific features have been provided, the catheter connector of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

What is claimed as new and desired to be protected by Letters Patent of the United States is:

1. A catheter connector, comprising:
a body comprising a cannula and a tail, said cannula extending from a distal end of said body and including a blunt distal end configured for insertion into a proximal end of a catheter following placement of a distal end of the catheter in a patient, said tail extending from a proximal end of said body configured for insertion into a distal end of a tube, wherein said body establishes fluid communication between the tube and the catheter;
a securement device comprising mating portions configured to secure said catheter to said body by locking together directly around said catheter following insertion of the cannula into the catheter, the securement device having a first position wherein the mating portions are not locked around the catheter, and a second position wherein the mating portions are locked around the catheter, the securement device is attached to the distal end of the body in both the first and second positions; and
a winged covering apparatus positioned over at least a portion of said body.

2. The catheter connector according to claim 1, wherein said body and said securement device are unitary.

3. The catheter connector according to claim 2, wherein said securement device is attached to said body by a living hinge.

4. The catheter connector according to claim 1, wherein said body further comprises a ribbed region.

5. The catheter connector according to claim 1, wherein said cannula is comprised of metal.

6. The catheter connector according to claim 1, wherein said tail comprises a barbed end.

7. The catheter connector according to claim 1, wherein the blunt distal end of said cannula comprises a rounded edge.

8. The catheter connector according to claim 1, wherein said mating portions are connected by a living hinge.

9. The catheter connector according to claim 1, wherein said mating portions comprise catheter receiving portions having distal ends that are funneled outward.

10. The catheter connector according to claim 1, wherein said mating portions comprise catheter receiving portions that together accommodate said catheter when closed therearound so that a tight seal is formed between said catheter receiving portions and said catheter.

11. The catheter connector according to claim 1, wherein said mating portions comprise locking portions having rounded distal ends.

12. The catheter connector according to claim 1, wherein said winged covering apparatus is made of silicone.

13. The catheter connector according to claim 1, wherein said body further comprises a region having a non-uniform outer surface, said winged covering apparatus comprising an inner surface configured to mesh with said non-uniform outer surface to prevent relative movement of said body with respect to said winged covering apparatus.

14. The catheter connector according to claim 1, wherein said body further comprises a head positioned at a distal end thereof, said cannula extending from said head.

15. The catheter connector according to claim 14, wherein said mating portions are separately attached to said body and comprise cut-away portions to receive said head therein.

16. The catheter connector according to claim 15, wherein said head is slightly smaller than said cut-away portions.

17. A catheter connector, comprising:
  a body comprising a cannula and a tail, said cannula extending from a distal end of said body and including a blunt distal end configured for insertion into a proximal end of a catheter following placement of a distal end of the catheter in a patient, said tail extending from a proximal end of said body configured for insertion into a distal end of a tube, wherein said body establishes fluid communication between the tube and the catheter;
  a securement device attached to the distal end of the body, comprising mating portions configured to secure said catheter to said body by locking together directly around said catheter following insertion of the cannula into the catheter, wherein said mating portions further comprise catheter gripping liners.

18. An assembly for connecting a catheter to extracorporeal medical equipment, comprising:
  a catheter connector comprising a body having a lumen therethrough and a securement device attached at two separate locations to said body at a distal end thereof, said securement device configured to secure a catheter to said body such that said body lumen is in fluid communication with said catheter;
  a tube connected at one end to a proximal end of said body and at an opposite end to a hub such that said body lumen is in fluid communication with said hub; and
  a covering positioned over at least a portion of said body and said tube, said covering being adapted for attachment to a patient.

19. The catheter connector according to claim 18, wherein said body includes a catheter receiving member extending from a distal end thereof.

20. The catheter connector according to claim 19, wherein the catheter receiving member includes a first and second cannula configured to receive a dual lumen catheter thereover.

21. The catheter connector according to claim 18, wherein said covering comprises winged portions.

22. The catheter connector according to claim 18, further comprising a sleeve to secure said tube to said hub.

* * * * *